(12) United States Patent
Fine et al.

(10) Patent No.: US 8,708,907 B2
(45) Date of Patent: Apr. 29, 2014

(54) METHOD AND APPARATUS FOR DETERMINING ONE OR MORE BLOOD PARAMETERS FROM ANALOG ELECTRICAL SIGNALS

(75) Inventors: Ilya Fine, Rehovot (IL); Alexander Kaminsky, Rehovot (IL)

(73) Assignee: Elfi-Tech, Rehovot (IL)

( * ) Notice: Subject to any disclaimer, the term of this patent is extended or adjusted under 35 U.S.C. 154(b) by 416 days.

(21) Appl. No.: 12/774,056

(22) Filed: May 5, 2010

(65) Prior Publication Data

US 2010/0286497 A1 Nov. 11, 2010

Related U.S. Application Data

(60) Provisional application No. 61/175,981, filed on May 6, 2009.

(51) Int. Cl.
*A61B 5/02* (2006.01)
*A61B 5/14551* (2006.01)
*A61B 5/145* (2006.01)
*A61B 8/06* (2006.01)
*A61B 8/12* (2006.01)
*A61B 5/026* (2006.01)

(52) U.S. Cl.
USPC ........... 600/369; 600/301; 600/323; 600/324; 600/336; 600/364; 600/368; 600/465; 600/467; 600/468; 600/504

(58) Field of Classification Search
CPC ..... A61B 5/026; A61B 5/0261; A61B 5/1455
USPC ......... 600/368, 369, 301, 323, 324, 336, 364, 600/465, 467, 468, 504
See application file for complete search history.

(56) References Cited

U.S. PATENT DOCUMENTS

| | | | | |
|---|---|---|---|---|
| 4,476,875 A | * | 10/1984 | Nilsson et al. | 600/479 |
| 5,219,962 A | | 6/1993 | McDaniel et al. | |
| 5,284,149 A | * | 2/1994 | Dhadwal et al. | 600/476 |
| 5,598,841 A | * | 2/1997 | Taniji et al. | 600/342 |

(Continued)

FOREIGN PATENT DOCUMENTS

| | | |
|---|---|---|
| WO | WO2007113804 | 10/2007 |
| WO | WO2007144880 | 12/2007 |
| WO | WO2008053474 | 5/2008 |

OTHER PUBLICATIONS

PCT Search report of PCT/US10/56282.

(Continued)

*Primary Examiner* — Jacqueline Cheng
*Assistant Examiner* — Puya Agahi
(74) *Attorney, Agent, or Firm* — Marc Van Dyke; 4th Dimension IP

(57) ABSTRACT

Embodiments of the present invention relate to a system and method for in vivo measurement of blood parameters by processing analog electrical signals from a plurality of photodetectors. In some embodiments, it is possible to determine one or more blood parameters according to (i) a first electrical signal from a first detector and (ii) a second electrical signal from a second photodetector. A difference analog electrical signal is generated, indicative of a difference between the light response signal at the first location and light response signal at the second location, is generated. One or more blood parameters may be detected according to the difference analog electrical signal.

12 Claims, 14 Drawing Sheets

(56) References Cited

U.S. PATENT DOCUMENTS

| | | | |
|---|---|---|---|
| 5,817,025 A * | 10/1998 | Alekseev et al. | 600/477 |
| 6,259,936 B1 * | 7/2001 | Boggett et al. | 600/310 |
| 6,263,227 B1 * | 7/2001 | Boggett et al. | 600/407 |
| 2002/0077535 A1 | 6/2002 | Finarov et al. | |
| 2002/0173709 A1 | 11/2002 | Fine et al. | |
| 2003/0069487 A1 | 4/2003 | Mortara | |
| 2003/0137650 A1 | 7/2003 | Fine et al. | |
| 2004/0000242 A1 | 1/2004 | Simeth | |
| 2004/0176671 A1 | 9/2004 | Fine et al. | |
| 2004/0225205 A1 | 11/2004 | Fine et al. | |
| 2004/0249252 A1 | 12/2004 | Fine et al. | |
| 2005/0101846 A1 | 5/2005 | Fine et al. | |
| 2006/0009685 A1 | 1/2006 | Finarov et al. | |
| 2006/0129040 A1 | 6/2006 | Fine et al. | |
| 2006/0200014 A1 | 9/2006 | Fine et al. | |
| 2007/0078312 A1 | 4/2007 | Fine et al. | |
| 2007/0232940 A1 | 10/2007 | Fine et al. | |
| 2009/0082642 A1 | 3/2009 | Fine | |
| 2009/0091741 A1 * | 4/2009 | Dogariu | 356/39 |
| 2009/0209834 A1 | 8/2009 | Fine | |
| 2009/0209934 A1 | 8/2009 | Domkowski et al. | |
| 2010/0286497 A1 | 11/2010 | Fine et al. | |
| 2011/0033385 A1 | 2/2011 | Fine et al. | |
| 2011/0082355 A1 | 4/2011 | Eisen et al. | |
| 2012/0130215 A1 | 5/2012 | Fine et al. | |

OTHER PUBLICATIONS

PCT Search opinion of PCT/US10/56282.
U.S. Appl. No. 12/431,469 through Aug. 25, 2012.
USPTO office action (Non-final rejection) for U.S. Appl. No. 13/292,110—office action was mailed on Nov. 21, 2013.

* cited by examiner

METHOD AND APPARATUS FOR DETERMINING ONE OR MORE BLOOD PARAMETERS FROM ANALOG ELECTRICAL SIGNALS

CROSS-REFERENCE TO RELATED APPLICATIONS

This patent application claims the benefit of U.S. Provisional Patent Application No. 61/175,981, filed May 6, 2009 and incorporated herein by reference in its entirety.

FIELD OF THE INVENTION

The present invention relates to a system and method for in vivo measurement of biological parameters of a mammalian subject (for example, a human) related to blood rheology and/or hemostasis. In particular, the present invention relates to a system and method for in vivo measurement of blood parameters by processing analog electrical signals from a plurality of photodetectors.

BACKGROUND AND RELATED ART

Near infrared spectroscopy (NIRS) is a well-established non-invasive technique which allows for the determination of tissue and blood analytes conditions based on spectro-photometric measurements in the visible and near-infrared regions of the spectrum of light. According to this technique, incident light penetrates the examined skin, and reflected and/or transmitted light is/are measured. In order to quantify any blood analyte, light of at least two different wavelengths is required. Optical plethysmography, pulse oximetry, and occlusion spectroscopy are the most prominent examples of usage of the NIR spectroscopy in medicine and physiological studies.

Visible or near infrared light is commonly used to track the optical manifestation of some time-dependent physiological processes. Such prolonged measurement of light response as a function of time can provide clinician with valuable information about time-dependent physiological processes.

For example, the measured light response of a natural heart beat pulsation is varied with each pulse. The signal is then measured at one point of the pulse wave and compared with the signal at another point. The difference between the values is due to arterial blood alone. In the pulse-oximetry, this phenomenon is utilized for the determination of oxy-hemoglobin saturation.

In the case of occlusion spectroscopy, the optical time-dependent signal is originated by light scattering changes associated with the red blood cells (RBC) aggregation process. In this case, the optical signal changes are utilized for the hemoglobin or glucose measurement.

Yet another known method enables to generate the required changes is the application of a periodic or non-periodic local pressure variation, resulting in blood volume fluctuations. These fluctuations are used to measure different blood parameters, like hemoglobin or glucose.

The major underlying assumption in the processing of all kind of the time-dependent signals is that the measured optical variation is originated solely by blood related components. In pulse oximetry, for example, it's commonly accepted that arterial blood volume changes are the only responsible factor staying behind the optical signal modulation. However, a more complex physical analysis shows that even if the only changes in the system are ascribed to the blood, the measured optical response of these changes is a convolution of absorption and scattering properties of blood and surrounding media. While carrying out any algorithmic modeling and signal processing procedure of these measured optical signals, the tissue related effects can not be disregarded. Therefore, the common denominator of all time-dependent signal related optical methods relies on the measurement of optical responses originated by the blood dynamics or hemorheological status changes.

It should be noted that the accuracy of time-dependent methods depends on the ability to identify the hemorheological component of the blood. For example, in the particular case of pulse-oximetry, the heart beats modulate the hemorheological status of circulating blood, resulting in the fluctuation of RBC velocity, which is associated with the shear forces changes. The variation of the hemorheological blood parameters enables to optically distinguish the pulse-related changes of the signal. Therefore, the decreased accuracy in the determination of hemorheological properties leads to a lower accuracy in the determination of the sought blood parameter. Among the blood parameters which can be derived from the hemorheological changes are hemoglobin oxygen saturation, carohyhemoglobin (percentage of HbCO out of total hemoglobin), hemoglobin blood concentration and/or glucose.

Moreover, the arterial blood pressure is another physiological parameter, which is commonly derived from the hemorheological related variations. The systolic blood pressure can be determined with assistance of inflating cuff which induces hemorheological variations artificially. When a pressure beyond the systolic pressure is applied, no pulsatile waveform appears at the down-flow. The diastolic point of the pressure is frequently measured by using Korotkoff's sounds. The source of these sounds is associated with abrupt changes in hemorheological properties of blood, occurring due to deflation of cuff from the systolic point. These hemorheological changes, in the vicinity of the diastolic point, result in a very typical pattern of sound, which can be detected by a stethoscope or by other acoustic device. However, the sound related method is very sensitive to different motion artifacts and therefore in automatic blood pressure devices, commonly used for the self-monitoring, the accuracy of blood pressure reading is impaired.

The following published patent documents provide potentially relevant background art, and are each incorporated herein by reference in their entirety: WO 2007/144880 and WO 2007/113804

SUMMARY OF EMBODIMENTS

An apparatus for obtaining physiological information from a subject the apparatus comprises: a) one or more light sources configured to apply partially or entirely coherent light to a target region of the subject to induce a light response signal from the illuminated target region; b) a detection system including: a) a first photodetector configured to detect the light response signal prevailing at a first location to generate a first photodetector analog electrical signal; b) a second photodetector configured to detect the second light response signal prevailing at a second location to generate a second photodetector analog electrical signal, the second location being offset from the first location by an offset distance that is at least 0.1 mm and at most 2 cm; c) an analog electronics assembly configured to generate, from the first and second analog electrical signals, a difference analog electrical signal that is indicative of a difference between the light response signal at the first location and at the second location (in some embodiments, the difference analog signal is indicative of a difference between a light field prevailing at the first location and a light field prevailing at the second location); d) a digitizer (i.e. A to D converter) for digitizing the difference analog electrical signal to generate a digitized signal; and e) a digital processing unit operative to receive and analyze the digitized signal to compute at least one physiological parameter of the subject.

In some embodiments, the apparatus further comprises: g) a pressurizing assembly operative to induce a change in blood flow at or near the target region by applying a pressure or a force to the subject's skin.

In some embodiments, this may be useful for determining a blood rheological parameter. For example, this may be useful for determining systolic blood pressure to thereby determine RBC aggregation—for example, a rate of aggregation of an average particle size—the skilled artisan is directed to WO 2008/053474 for details.

In some embodiments, the pressurizing assembly includes: i) a strap for constricting blood flow in a subject's finger; and ii) a pneumatic tube for tightening the strap around the subject's finger to constrict the blood flow.

In some embodiments, the pressurizing assembly is operative to create an intermittent blood stasis state by applying over systolic blood pressure to the subject, thereby enabling determination of red blood cell (RBC) aggregation.

In some embodiments, the digital processing unit is configured: (i) to detect stochastic time-dependent fluctuations in a magnitude of the difference analog electrical signal; and (ii) to compute the at least one physiological parameters in accordance with the detected stochastic fluctuations.

In some embodiments, the digital processing unit is operative to compute a blood velocity and/or blood rheology parameter from the digitized signal.

In some embodiments, the digital processing unit is operative to compute from the digitized signal at least one parameter selected from the group consisting of a blood viscosity, a blood particle size (for example, a central tendency such as an average of RBC aggregates) and a blood coagulation rate.

In some embodiments, the first photodetector is situated at the first location and the second photodetector is situated at the second location, and a distance between the first and second detectors is the offset distance.

In some embodiments, i) the first and/or second photodetectors are respectively situated away (for example, separated by at least 1 cm or 2 cm or 5 cm or more) from the first and second locations and respectively receive light respectively from the first and/or second location via an optical fiber.

In some embodiments, the digital processing unit is operative to effect at least one of (i) a temporal autocorrelation analysis of the digitized signal; (ii) effecting a power spectrum analysis of the digitized signal, wherein the at least one physiological parameter is computed in accordance with results of the temporal autocorrelation and/or power spectrum analysis.

In some embodiments, the analog electronics assembly: i) is configured to receive: A) a first input analog signal derived from the first analog photodetector analog electrical signal; and B) a second input analog signal derived from the second analog photodetector analog electrical signal; and ii) to generate the difference analog electrical signal from a difference between the first and second input signals.

In some embodiments, the one or more light sources are part of an "illuminating system" which may include one or more optical components for example, for focusing the coherent light.

There is no limitation on the wavelength of coherent light that may be used. In some embodiments, the coherent light may include wavelengths between 350 nm and 2,000 nm, for example, visible (for example, red) and/or near infra-red (NIR) light.

In one non-limiting example, the coherent light is red and/or NIR light which may be useful for determining a light of read and blood oxygen saturation and/or a blood hemoglobin concentration.

There is no limitation on the type of photodetector that may be used. In one non-limiting example, the first and/or second photodetector is a Charge-coupled devices (CCD).

A method for obtaining physiological information from a subject in accordance with a light field whose intensity varies according to location is now disclosed. The method comprises: a) applying partially or entirely coherent light to a target region of the subject to induce a light response signal from the illuminated target region which contributes to a location-dependent light field; b) detecting a light field signal prevailing at a first location to generate a first analog signal, the first analog signal including a DLS component that is indicative of a first dynamic light scattering (DLS) measurement; c) detecting a light field signal prevailing at a second location to generate a second analog signal including a DLS component that is indicative of a second dynamic light scattering (DLS) measurement a ratio and that is uncorrelated to the DLS component of the first analog signal; d) processing the first and second analog signals to generate a processed analog signal including a DLS component that is indicative of a combination of the first and second dynamic scattering measurements wherein a ratio between: i) a boosted DLS contribution ratio between a magnitude of the DLS component of the processed analog signal and the magnitude of the processed analog signal; and ii) at least one of a first DLS contribution ratio and a second DLS contribution ratio, is at least 10 and wherein: i) the first DLS contribution ratio is defined as a ratio between a magnitude of the DLS component of the first analog signal and the magnitude of the first analog signal; and ii) the second output ratio is defined as a ratio between a magnitude of the DLS component of the second analog signal and the magnitude of the second analog signal.

In some embodiments, the method further comprises: e) digitizing the processed analog signal to generate a digital signal indicative of a combination of the first and second dynamic scattering measurements; and f) processing the indicative digital signal to compute at least one physiological parameter.

In some embodiments, the computing includes computing at least one of a blood velocity, a blood rheological parameter, a blood pressure, a heartbeat, a blood oxygen concentration, and a pulse.

In some embodiments, the method further comprises: e) before the light field detecting, inducing a change in blood flow at or near the target region.

In some embodiments, the blood flow change inducing is carried out by applying a force or a pressure to the subject.

In some embodiments, the target region is located in a location selected from the group consisting of a finger region, a back region, a leg region, a face region and an arm region.

In some embodiments, the method is carried out so that the first output ratio and/or the second output ratio is at most 0.05

In some embodiments, the method is carried out such that an ambient light component (for example, at one or more specified wavelengths—for example, the wavelength of the coherent light) of the detected light field signal prevailing at the first location is substantially equal to and/or correlated with an ambient light component of the detected light field signal prevailing at the second location.

In some embodiments, the method is carried out such that a slowly-varying component of the detected light field signal prevailing at the first location is substantially equal to and/or correlated with an slowly-varying component of the detected light field signal prevailing at the second location.

In some embodiments, the method is carried out such that a rapidly-varying non-stochastic rapidly-varying component of the detected light field signal prevailing at the first location is substantially equal to a non-stochastic rapidly-varying component of the detected light field signal prevailing at the second location.

In some embodiments, the method is carried out so that a ratio between an intensity, at a wavelength of the at least partially coherent light, of the detected light field signal prevailing at the first location and intensity, at a wavelength of the at least partially coherent light, of the detected light field signal prevailing at the second location is between 0.95 and 1.05.

DETAILED DESCRIPTION OF EMBODIMENTS

Figure 1:
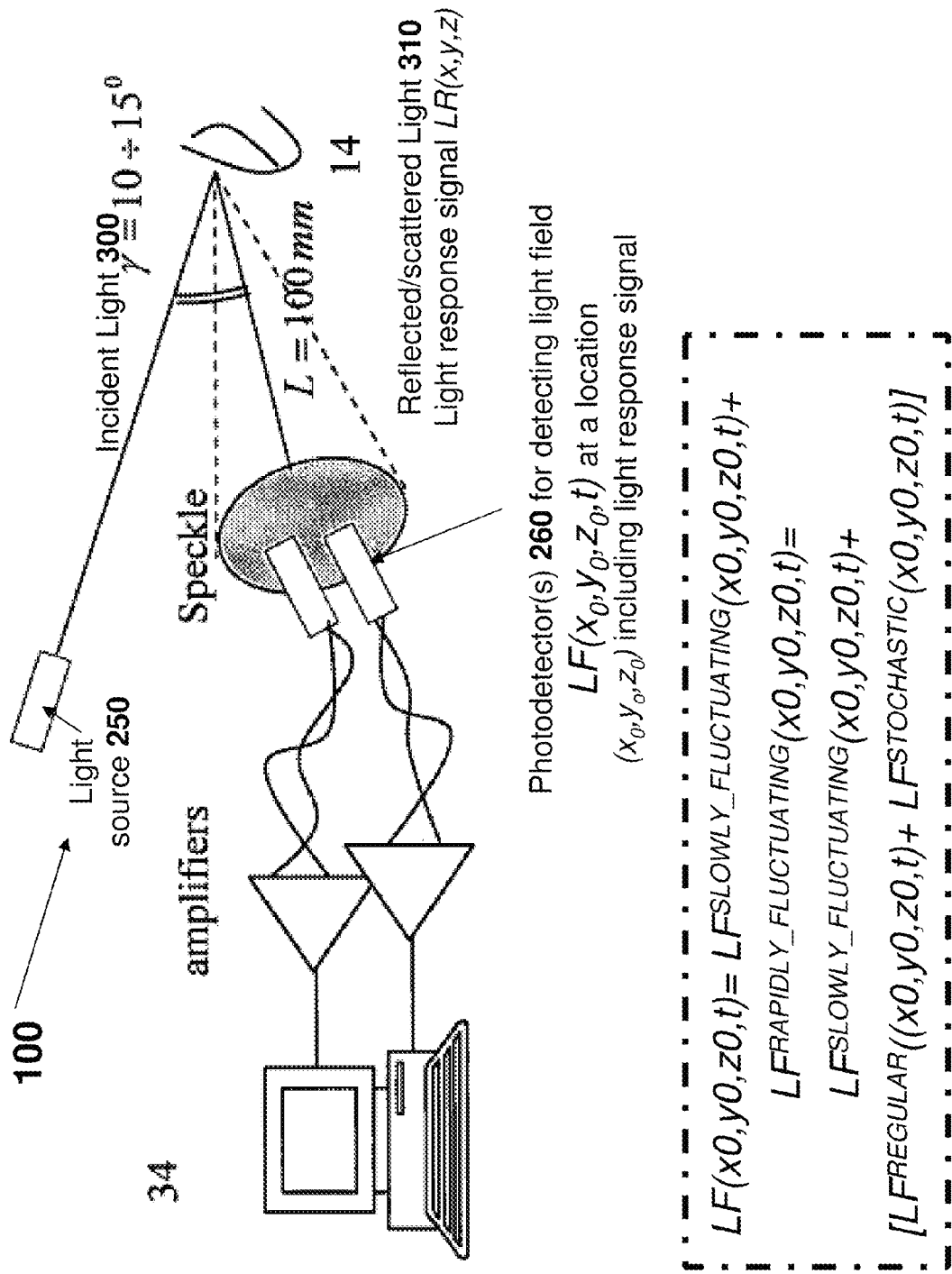
FIG. 1 is an illustration of a DLS measurement based system for measuring one or more blood parameters (reproduced from WO 2008/053474).

The claims below will be better understood by referring to the present detailed description of example embodiments with reference to the figures. The description, embodiments and figures are not to be taken as limiting the scope of the claims. It should be understood that not every feature of the presently disclosed methods and apparatuses for handling error correction is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to'), rather than the mandatory sense (i.e. meaning "must").

WO 2008/053474, incorporated herein by reference in its entirety, discloses a system and method for in vivo measurement of biological parameters.

In particular, WO 2008/053474 discloses a novel optical technique suitable for the in vivo measurement in a subject utilizing dynamic light scattering (DLS) approach. The effect of DLS are utilized for the measurement of variety of blood related parameters, such as viscosity of the blood and blood plasma, blood flow, arterial blood pressure and other blood chemistry and rheology related parameters such as concentration of analyte (e.g. glucose, hemoglobin, etc.), oxygen saturation etc.

DLS is a well-established technique to provide data on the size and shape of particles from temporal speckle analysis. When a coherent light beam (laser beam, for example) is incident on a scattering (rough) surface, a time-dependent fluctuation in the scattering property of the surface and thus in the scattering intensity (transmission and/or reflection) from the surface is observed. These fluctuations are due to the fact that the particles are undergoing Brownian or regular flow motion and so the distance between the particles is constantly changing with time. This scattered light then undergoes either constructive or destructive interference by the surrounding particles and within this intensity fluctuation information is contained about the time scale of movement of the particles. The scattered light is in the form of speckles pattern, being detected in the far diffraction zone. The laser speckle is an interference pattern produced by the light reflected or scattered from different parts of an illuminated surface. When an area is illuminated by laser light and is imaged onto a camera, a granular or speckle pattern is produced. If the scattered particles are moving, a time-varying speckle pattern is generated at each pixel in the image. The intensity variations of this pattern contain information about the scattered particles. The detected signal is amplified and digitized for further analysis by using the autocorrelation function (ACF) technique. The technique is applicable either by heterodyne or by a homodyne DLS setup.

The kinetics of optical manifestations of two kinds of physiological signals is measured in vivo: the pulsatile signal associated with heart beats and the post-occlusion optical signal which is induced by an artificially generated blood flow cessation. The light transmission and/or reflection signals are used as a control of the physiological response. This kind of control measurement can be carried out simultaneously with the DLS reflection measurement. The mutual correspondence between DLS and standard optical signals is subject to a comparison analysis.

FIG. 1, reproduced from WO 2008/053474, is an illustration of a DLS measurement based system for measuring one or more blood parameters. System 100 includes a light source unit 250 (e.g. laser) for generating at least partially coherent light; optical arrangement (not shown) including focusing optics and possibly also collecting optics; and a detection unit including a photodetector 260. A focused beam of light 300 produced by laser 250 (e.g., a semiconductor laser) is used as a localized light source. In a non-limiting example, a light source unit 250 may be a laser diode (650 nm, 5 mW) or VCSEL (vertical cavity surface emitting laser). The light response i.e. the reflected and/or transmitted light returned from the localized region of the subject's surface 14 (subject's finger in the present example) illuminated with the localized light source 250, can be collected in a determined distance L (in a non-limiting example, L=100 mm) either directly by a detector or via multimode fiber optics. In a non-limiting example, the multimode fiber optics may be a bi-furcated randomized optical fiber where one optical entrance is connected to the detector and another one is optically coupled with the laser diode. In particular, as shown in FIG. 1, system 100 includes at least one laser diode and at least one photodetector (for example, photodiode(s)) appropriately positioned in the reflection-mode measurement set-up.

The photodetector 260 is positioned in space at location (x0,y0,z0) and is configured to detect a light field $LF(x_0, y_0, z_0)$—i.e. the light field that exists/prevails at point $(x_o, y_o, z_o)$. Typically, the light detected by photodetector 260 comes from a number of sources including but not limited to (A) reflected light 310 which is reflected from and/or scattered by the biological tissue; and (ii) ambient light. Thus, it is possible to write:

$$LF(x_0, y_0, z_0) = LF_{reflected}(x_0, y_0, z_0) + LF_{ambient}(x_0, y_0, z_0) + \text{other terms(s)} \quad (EQ. 1)$$

Throughout the present disclosure, LF denotes a light field.

When light from light source 250 is incident upon biological tissue, (i) a first portion of the incident light is reflected from or scattered from "Brownian particles" (i.e. particles undergoing Brownian motion within a liquid—for example, red blood cells or thrombocytes) to generate a first light response signal whose magnitude/intensity varies stochastically and rapidly in time—this first light response signal is referred to as $LF_{reflected\_brownian}(x_0, y_0, z_0)$; (ii) a second portion of the incident light is reflected from stationary biological matter other than Brownian particles—for example, from skin cells, etc—this second portion of the incident light generates a second light response signal whose magnitude/intensity varies at most "slowly" and/or is not stochastic in time—this second light response signal is referred to as $LF_{reflected\_non\_brownian}(x_0, y_0, z_0)$;

Thus, it is possible to write:

$$LF_{reflected}(x_0, y_0, z_0) = LF_{reflected\_non\_brownian}(x_0, y_0, z_0) + LF_{reflected\_brownian}(x_0, y_0, z_0) + \text{other term(s)} \quad (EQ. 2)$$

In Some Embodiments, $LF_{reflected\_brownian}(x_0, y_0, z_0)$ is indicative of a dynamic light scattering parameter. Unfortunately, in many clinical situations $$\frac{LF_{reflected\_brownian}(x_0, y_0, z_0)}{LF(x_0, y_0, z_0)}$$

and/or $$\frac{LF_{reflected\_brownian}(x_0, y_0, z_0)}{LF_{reflected\_non\_brownian}(x_0, y_0, z_0)}$$

and/or $$\frac{LF_{reflected\_brownian}(x_0, y_0, z_0)}{LF_{reflected\_ambient}(x_0, y_0, z_0)}$$

is "small" (for example, less than 0.1 or less than 0.01 or even smaller).

Embodiments of the present invention relate to apparatus and methods for "boosting" the relative contribution to an analog electrical signal of a component indicative of a dynamic light scattering measurement—for example, boosting the relative contribution of an analog electrical signal indicative of $LF_{reflected\_brownian}(x_0, y_0, z_0)$.

It is noted that, typically, $LF_{ambient}(x_0, y_0, z_0)$ (see Eqn. 1) and $LF_{reflected\_non\_brownian}(x_0, y_0, z_0)$ (see Eqn. 2) have an intensity that is either: (i) "slowly" fluctuating (for example, substantially constant or fluctuating at a rate less than 50 HZ); and/or (ii) "regularly behaved" and non-stochastic. One example of a "rapidly" fluctuating light signal that is regularly behaved and non-stochastic is light from a fluorescent light bulb operating at 50 HZ or 60 HZ. In contrast, the intensity of "speckles pattern light signal" $LF_{reflected\_brownian}(x_0, y_0, z_0)$ varies stochastically and rapidly—i.e. at a rate that is at least 50 HZ or at least 100 HZ or at least 200 HZ, depending on diffusion coefficient of the Brownian particle.

Thus, it is possible to write:

$$LF(x_0, y_0, z_0) = LF_{slowly\_fluctuating}(x_0, y_0, z_0) + \underbrace{[LF_{regular}(x_0, y_0, z_0) + LF_{stochastic}(x_0, y_0, z_0)]}_{rapidly-fluctuating} + \text{other terms} \quad (EQ. 3)$$

where (i) $LF_{slowly\_fluctuating}(x_0, y_0, z_0)$ is due to ambient light $LF_{ambient}(x_0, y_0, z_0)$ and/or light reflected from biological tissue other than Brownian particles $LF_{reflected\_non\_bownian}(x_0, y_0, z_0)$; (ii) rapidly-fluctuating (i.e. at a rate of greater than 50 HZ and/or 100 HZ and/or 200 HZ) $LF_{regular}(x_0, y_0, z_0)$ is due to ambient light $LF_{ambient}(x_0, y_0, z_0)$; and $LF_{stochastic}(x_0, y_0, z_0) = LF_{reflected\_brownian}(x_0, y_0, z_0)$/

For the present disclosure, "slowly fluctuating" refers to fluctuations at a rate of less than 50 HZ, while "rapidly fluctuating" refers to regular or stochastic fluctuations at a rate that exceeds 50 HZ (for example, at least 100 HZ or at least 200 HZ).

It is noted that: (i) $LF_{stochastic}(x_0, y_0, z_0)$ is the portion of $LF(x_0, y_0, z_0)$ that may be subjected to DLS analysis to yield one or more blood-related parameters; and (ii) in most clinical situations, $$\frac{LF_{stochastic}(x_0, y_0, z_0)}{LF(x_0, y_0, z_0)}$$

is relatively "small" (for example, less than 0.1 or less than 0.01 or even smaller).

Figure 2:
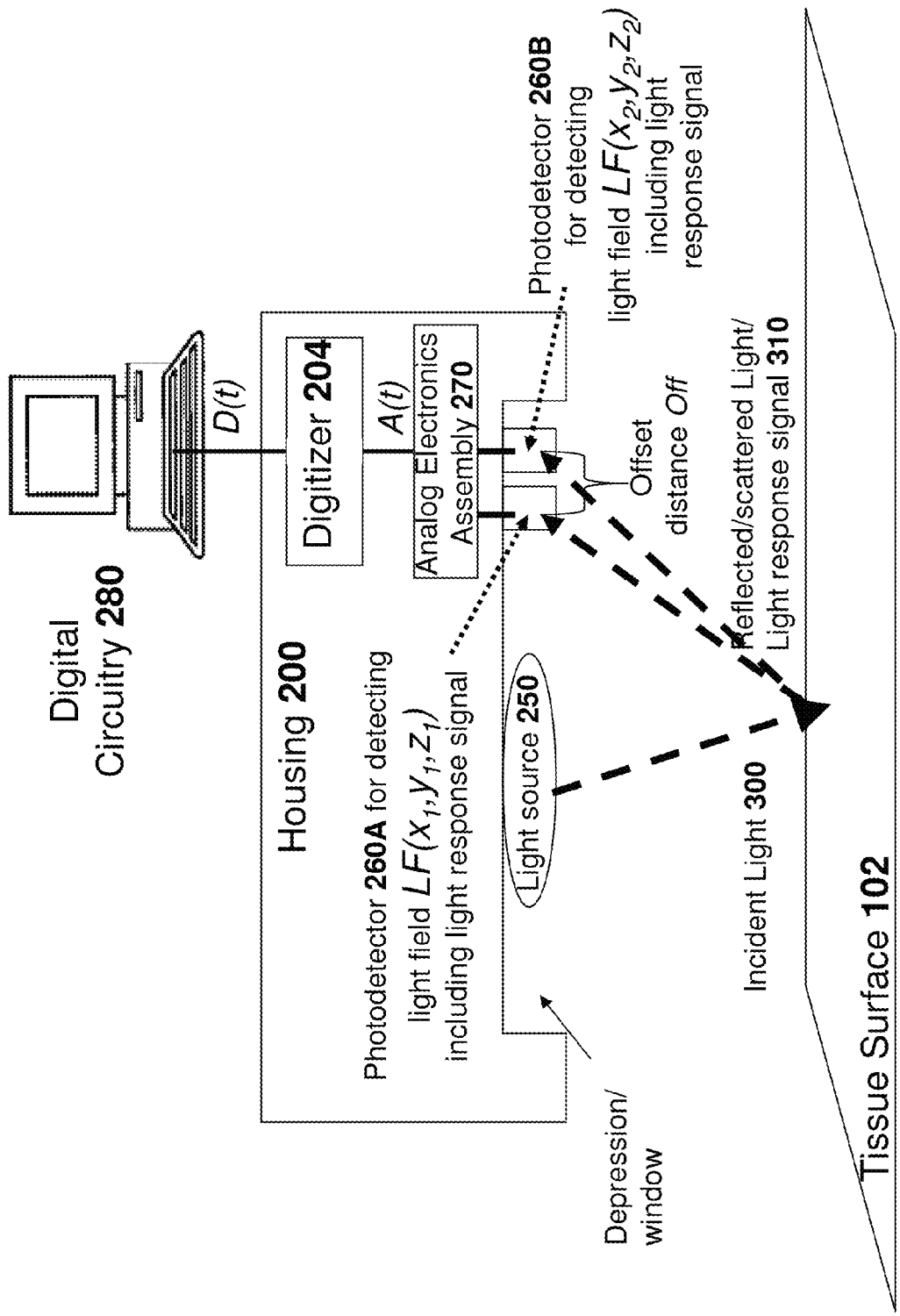
FIG. 2 is an illustration of a system for generating an analog electrical signal A(t).
Figure 3A:
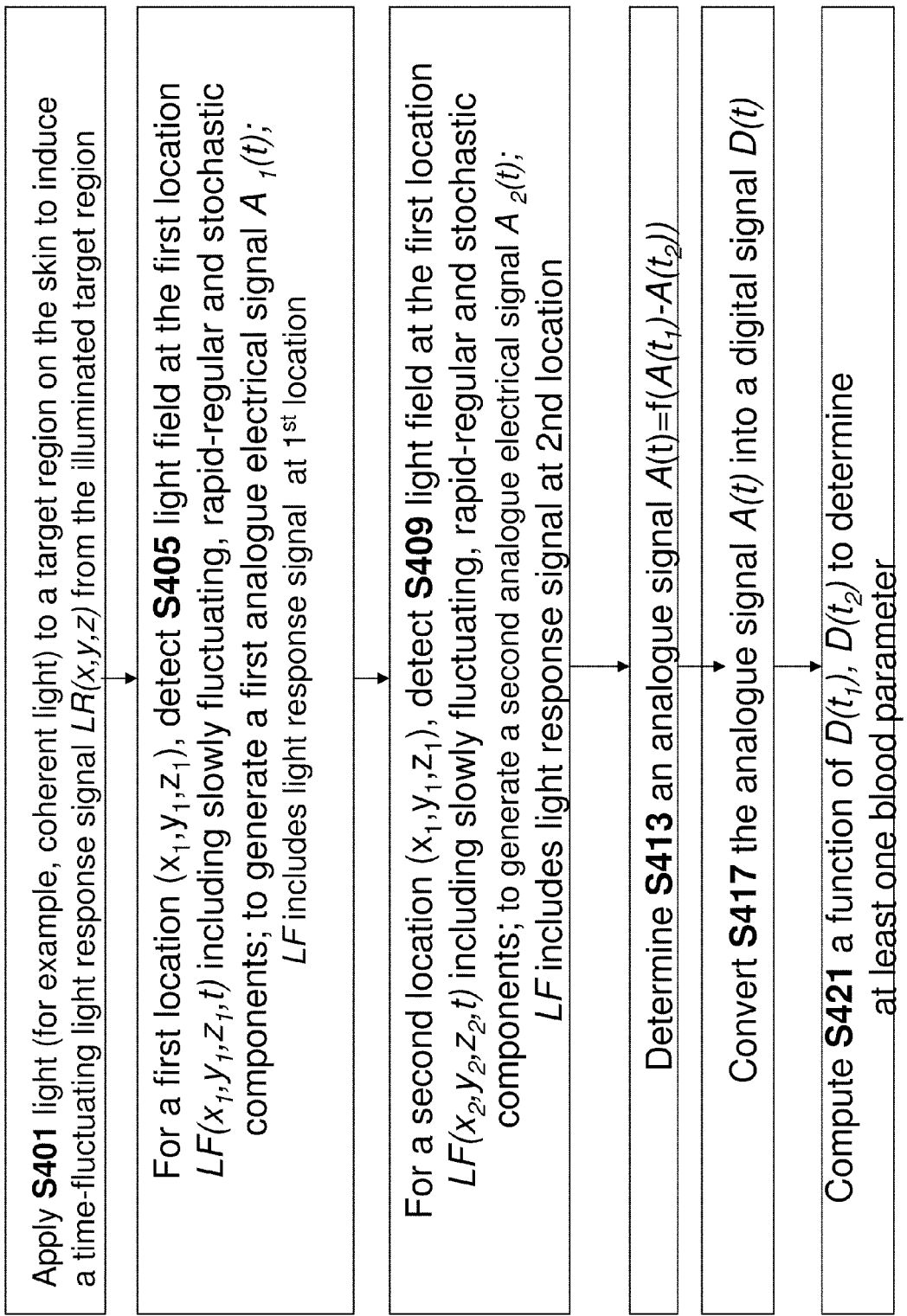
FIGS. 3A-3B and 7A-7B are flow charts of routines for determining at least one blood parameter according to some embodiments.
Figure 3B:
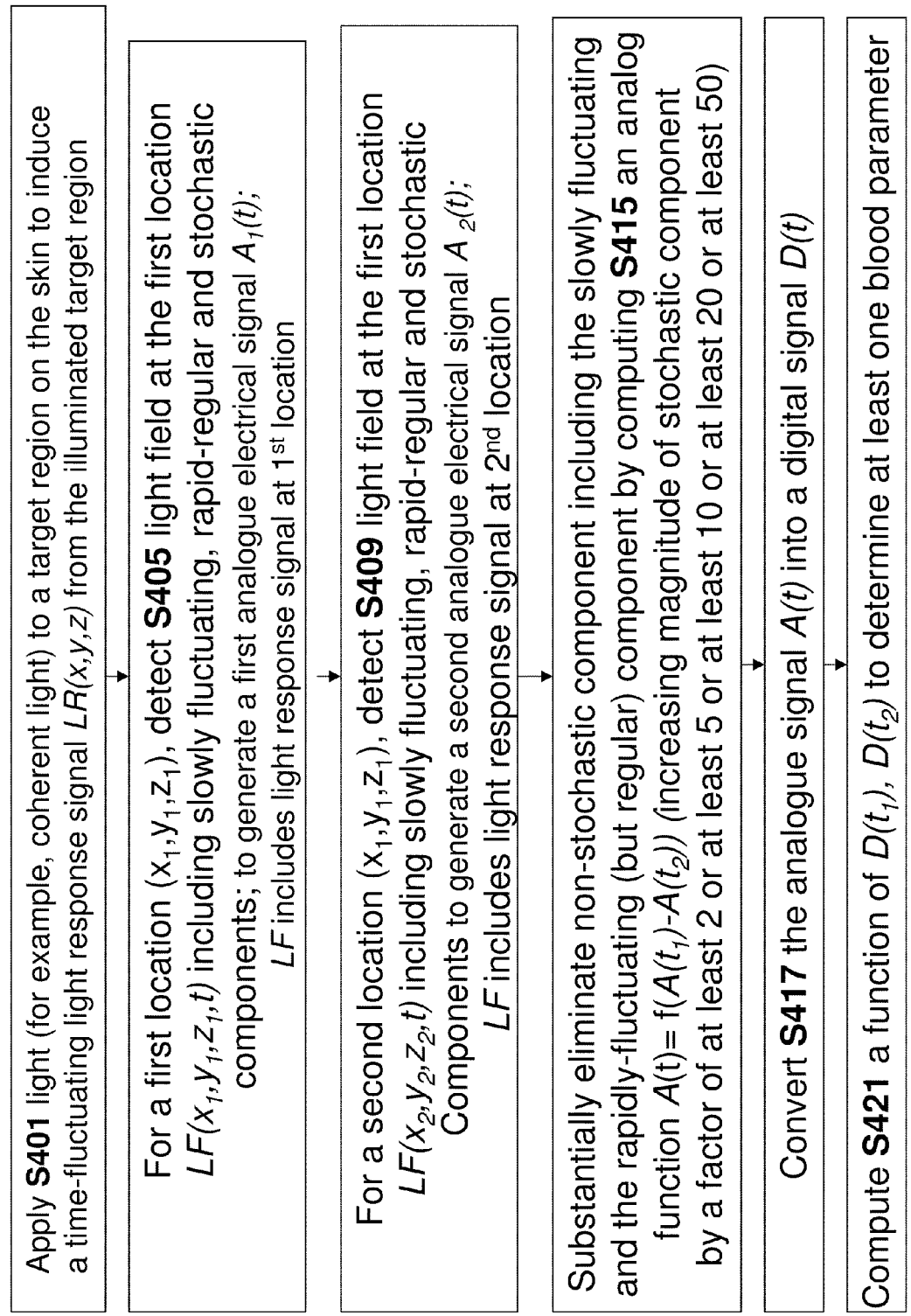
Figure 4:
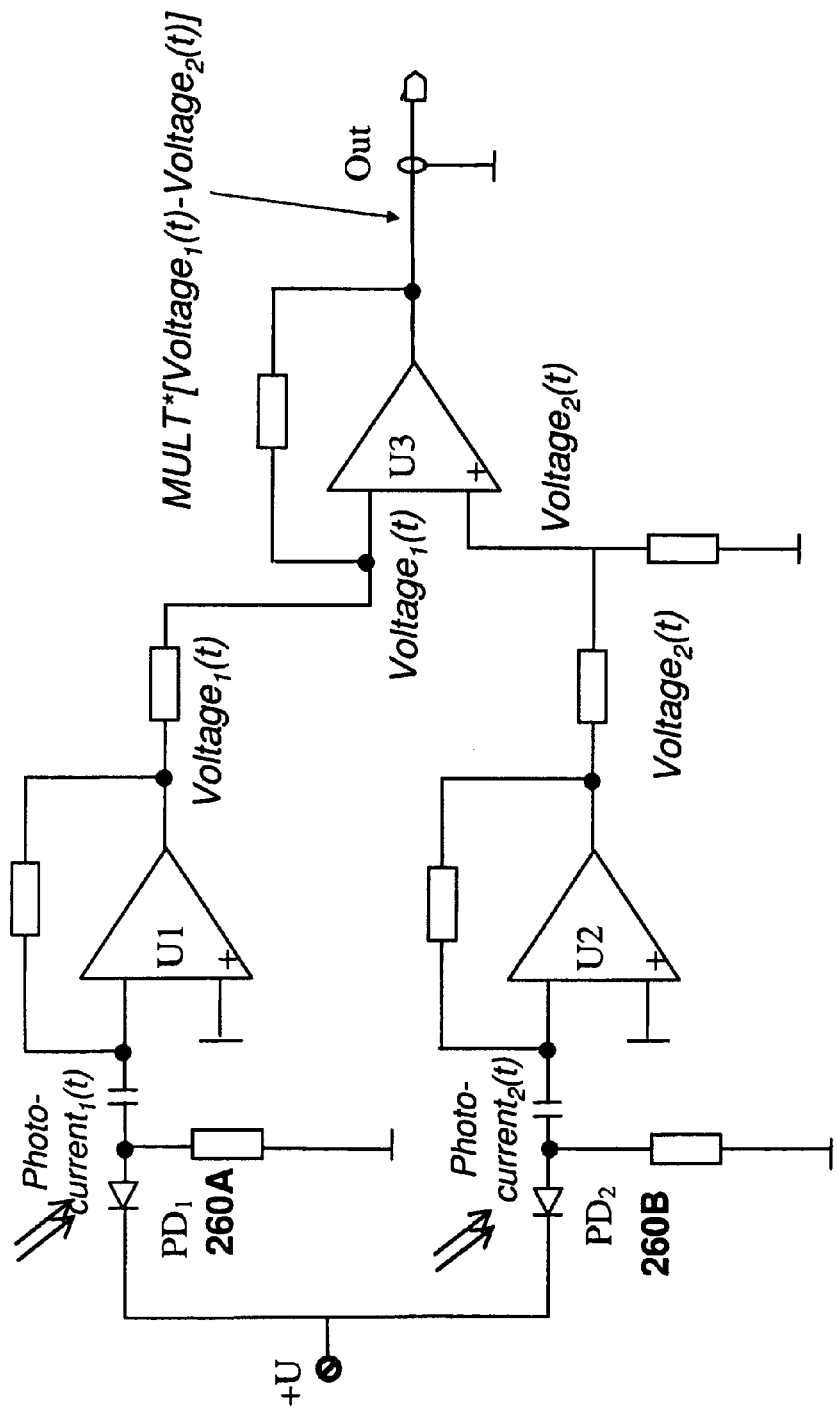
FIG. 4 is a circuit diagram of an exemplary analog electronic assembly 270 in accordance with some embodiments.

A First Discussion of a System Including Two Closely-Coupled Photodetectors with Reference to FIGS. 2-4

FIG. 2 is an illustration of a system for generating an analog electrical signal A(t) that includes a relatively "large" component (for example, at least 0.01 or at least 0.1 or at least 0.2 or least 0.3 or at least 0.5 or least 0.8) that is indicative of a time-varying "speckles pattern light signal" received by one or more photo-detectors. This analog signal may be converted, using A to D converter or digitizer 204, into a digital signal D(t). The digital signal may be subjected to any analysis described in WO 2008/053474 by digital circuitry 280 to determine one or more blood parameters—for example, temporal autocorrelation or power spectrum techniques.

In a non-limiting example, the data is collected at 22 KHz sampling rate and 16-bit resolution, and then analyzed by digital circuitry 280.

In the system of FIG. 2, light is received and detected by a plurality of photodetectors including: (i) photodetector 260A for detecting the light field $LF(x_1, y_1, z_1)$ at location $(x_1, y_1, z_1)$; (ii) photodetector 260B for detecting the light field $LF(x_2, y_2, z_2)$ at location $(x_2, y_2, z_2)$. Photodetector 260A generates a first analog electrical signal $A_1(t)$ from $LF(x_1, y_1, z_1) z_1)$. Photodetector 260B generates a second analog electrical signal $A_2(t)$ from $LF(x_2, y_2, z_2)$. Analog electronics assembly 270 receives the first $A_1(t)$ and second $A_2(t)$ analog electrical signals, and generates a "difference" between these two signals $A_1(t)-A_2(t)$ to produce analog electrical signal A(t) which is digitized. Photodetectors 260B and 260B are positioned so that: (i) they are close enough together so that $LF_{ambient}(x_1, y_1, z_1) \approx LF_{ambient}(x_2, y_2, z_2)$, $LF_{reflected\_non\_brownian}(x_1, y_1, z_1) \approx LF_{reflected\_non\_brownian}(x_2, y_2, z_2)$, $LF_{slowly\_fluctuating}(x_1, y_1, z_1) \approx LF_{slowly\_fluctuating}(x_2, y_2, z_2)$ and $LF_{regular}(x_1, y_1, z_1) \approx LF_{regular}(x_2, y_2, z_2)$; and (ii) they are far enough from each other such that the rapidly fluctuating $LF_{stochastic}(x_1, y_1, z_1)$ and $LF_{stochastic}(x_2, y_2, z_2)$ are not correlated with each other.

Figure 10:
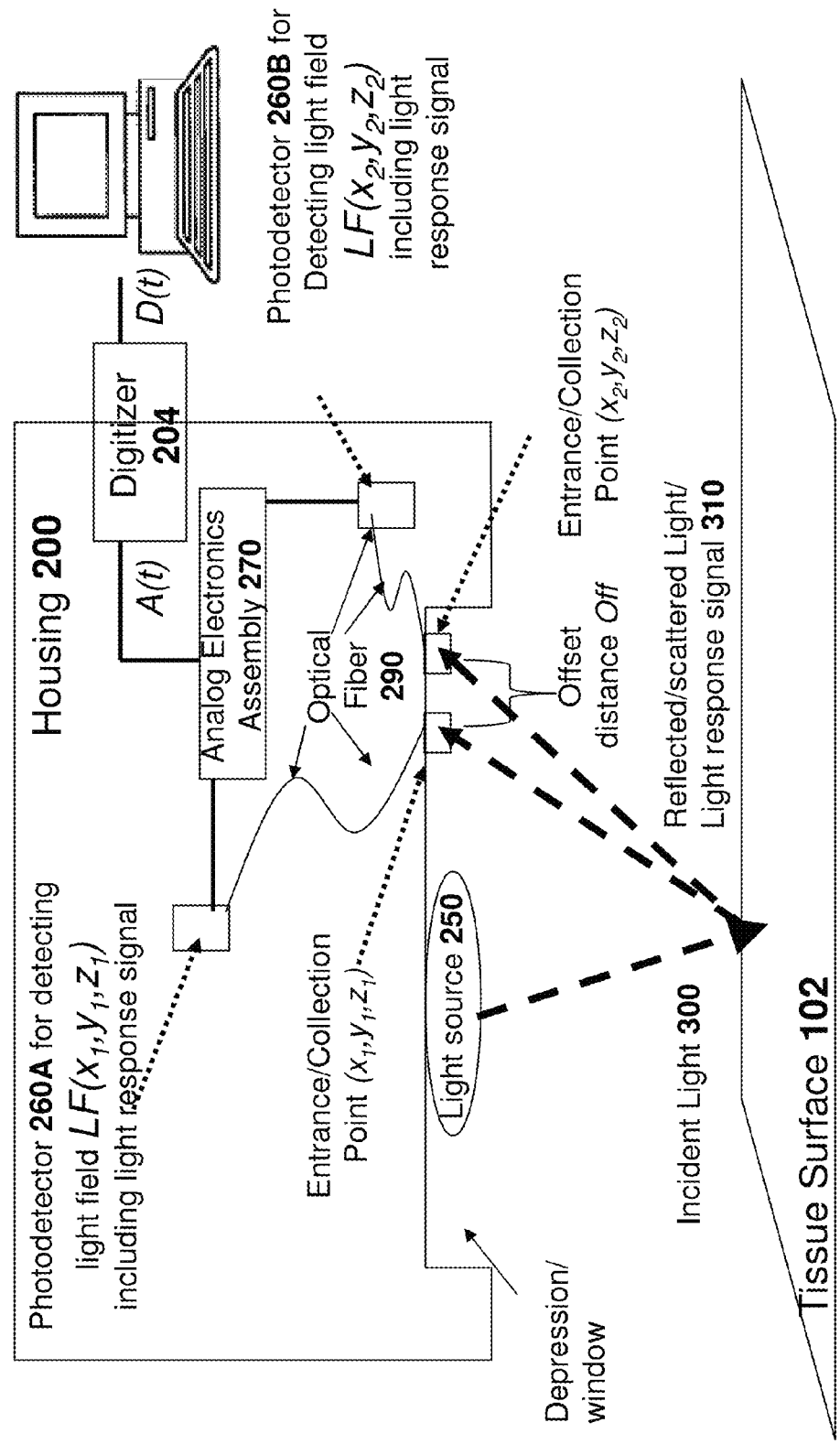
FIG. 10 illustrates an optical fiber-related embodiment.

In some embodiments, in order for $LF_{stochastic}(x_1, y_1, z_1)$ and $LF_{stochastic}(x_2, y_2, z_2)$ to be uncorrelated, $(x_1, y_1, z_1)$ and $(x_2, y_2, z_2)$ should be separated by at least 0.5 mm—i.e. the offset distance Off of FIGS. 2 and 10 should be at least 0.5 mm.

In some embodiments, in order for $LF_{reflected\_non\_brownian}(x_1, y_1, z_1) \approx LF_{reflected\_non\_brownian}(x_2, y_2, z_2)$, $LF_{slowly\_fluctuating}(x_1, y_1, z_1) \approx LF_{slowly\_fluctuating}(x_2, y_2, z_2)$ and $LF_{regular}(x_1, y_1, z_2) \approx LF_{regular}(x_2, y_2, z_2)$, then $(x_1, y_1, z_1)$ and $(x_2, y_2, z_2)$ should be separated by at most 10 cm or at most 5 cm or at most 3 cm or at most 2 cm or at most 1 cm—i.e. the offset distance Off of FIGS. 2 and 10 should be at most 10 cm or at most 5 cm or at most 3 cm or at most 2 cm or at most 1 cm.

In this case, if $A(t)=A_1(t)-A_2(t)$ represents $LF(x_1, y_1, z_1) - LF(x_2, y_2, z_2)$, then it is possible to write, using equation (3), that $A(t)$ represents $$[LF_{slowly\_fluctuating}(x_1, y_1, z_1) - LF_{slowly\_fluctuating}(x_2, y_2, z_2)] + \underbrace{\left\{ \begin{array}{l} [LF_{regular}(x_1, y_1, z_1) - LF_{regular}(x_2, y_2, z_2)] + \\ [LF_{stochastic}(x_1, y_1, z_1) - LF_{stochastic}(x_2, y_2, z_2)] \end{array} \right\}}_{rapidly-fluctuating}. \quad \text{Eq (4)}$$

In the special case where (i) exact equality prevails—i.e. $LF_{slowly\_fluctuating}(x_1, y_1, z_1)=LF_{slowly\_fluctuating}(x_2, y_2, z_2)$, $LF_{regular}(x_1, y_1, z_1)=LF_{regular}(x_2, y_2, z_2)$ and where (ii) rapidly fluctuating $LF_{stochastic}(x_1, y_1, z_1)$ and $LF_{stochastic}(x_2, y_2, z_2)$ are not correlated with each other, then $A(t)$ is a completely stochastic signal (i.e. indicative of a time-varying speckles pattern or DLS measurement produced by scattering from the Brownian particles), in contrast to $A_1(t)$ and $A_2(t)$ where the stochastic components of the signal may only be some fraction less than ½, for example, less than 0.1 or less than 0.01. Practically, $A(t)$ may also include some non-stochastic component. Nevertheless, in typical cases, the relative contribution of the non-stochastic component(s) (i.e., not due to scattering light on Brownian particles to generate a speckles pattern having a rapidly-varying intensity) to analog electric signal $A(t)$ is less than the contribution of respective non-stochastic components to $A_1(t)$ or $A_2(t)$.

A Discussion of a DLS Contribution Ratios

Consider the following ratios:

(i) a first DLS contribution ratio between (A) a magnitude of a "DLS component" of analog signal $A_1(t)$ (i.e. a component that is indicative of a DLS measurement—i.e. indicative of $LF_{stochastic}(x_1, y_1, z_1)$ or $LF_{Brownian}(x_1, y_1, z_1)$) and (B) $A_1(t)$, i.e.

$$\frac{\left| \begin{array}{l} \text{analog electrical component of } A_1(t) \\ \text{indicative of } LF_{Brownian}(x_1, y_1, z_1) \end{array} \right|}{|A_1(t)|} -$$

in many clinical situations, this first DLS ratio is at most 0.1 or at most 0.05 or at most 0.02 or at most 0.01, or even less.

(ii) a second DLS contribution ratio between (A) a magnitude of a "DLS component" of analog signal $A_2(t)$ (i.e. a component that is indicative of a DLS measurement—i.e. indicative of $LF_{stochastic}(x_2, y_2, z_2)$ or $LF_{Brownian}(x_2, y_2, z_2)$) and (B) $A_2(t)$, i.e.

$$\frac{\left| \begin{array}{l} \text{analog electrical component of } A_2(t) \\ \text{indicative of } LF_{Brownian}(x_1, y_1, z_1) \end{array} \right|}{|A_2(t)|} -$$

in many clinical situations, this second DLS ratio is at most 0.1 or at most 0.05 or at most 0.02 or at most 0.01, or even less.

(iii) a "boosted DLS contribution ratio" between (A) a magnitude of a "DLS component" of processed analog signal $A(t)$ (i.e. a component that is indicative of a DLS measurement(s)—i.e. indicative of a combination of (i) $LF_{stochastic}(x_1, y_1, z_1)$ or $LF_{Brownian}(x_1, y_1, z_1)$) and (ii) $LF_{stochastic}(x_2, y_2, z_2)$ or $LF_{Brownian}(x_2, y_2, z_2)$) and (B) $A_2(t)$, i.e.

$$\frac{\left| \begin{array}{l} \text{analog electrical component of } A(t) \\ \text{indicative of a combination of } LF_{Brownian}(x_1, y_1, z_1) \\ \text{and } LF_{Brownian}(x_2, y_2, z_2) \end{array} \right|}{|A_2(t)|}$$

in many clinical situations, this "boosted" DLS ratio exceeds the first and second DLS ratios is at least 0.05 or at least 0.1 or at least 0.2 or at least 0.5.

In some embodiments, a ratio between the "boosted DLS contribution ratio" and the "first DLS contribution ratio" and/or the "second DLS contribution ratio" is at least 3 or at least 5 or at least 10 or at least 20 or at least 50 or at least 100.

This "boosted ratio" may prevail for any length of time—for example, for at least 1 or 3 or 5 seconds.

It is now disclosed that, in some embodiments, the greater this "ratio" between the "boosted DLS contribution ratio" and the first and/or second DLS contribution ratio, the easier it is to utilize processed analog signal $A(t)$ to determine one or more physiological parameters, as the "Brownian" component is greater. This may obviate the need for signal amplification and/or the need for using a digitizer with "many" channels, allowing the use of a digitizer with "fewer" channels.

A Discussion of FIGS. 3A-3B

FIGS. 3A-3B are flow charts of routines for determining at least one blood parameter according to some embodiments. In step S401, light (for example, coherent light from light source 250) is applied to a target region of the biological tissue to induce a time-fluctuating light response signal from the illuminated target region. In step S405, a light field $LF(x_1, y_1, z_1)$ prevailing at a first location $(x_1, y_1, z_1)$ is determined to generate a first $A_1(t)$ analog electrical signal. In step S409, a light field $LF(x_2, y_2, z_2)$ prevailing at a second location $(x_2, y_2, z_2)$ is determined to generate a second $A_2(t)$ analog electrical signal. In step S413, an analogue signal $A(t)=A_1(t)-A_2(t)$ is determined. In step S417, this analog signal is converted into a digital signal (for example, by digitizer 204). In step S421, this digital signal is analyzed (for example, using any technique disclosed in WO 2008/053474—for example, one or more of temporal autocorrelation or power spectrum techniques) to compute one or more blood parameters.

FIG. 4 is a circuit diagram of an exemplary analog electronic assembly 270 in accordance with some embodiments. Photocurrent $Photocurrent_1(t)$—generated by the first photodetector 260A is converted by a "first cascade" operational amplifier U1 from a "current analog signal" $Photocurrent_1(t)$ to a "voltage analog signal" $voltage_1(t)$-$Photocurrent_1(t)$ and voltage$_1$(t) are non-limiting examples of "first analog signals" A$_1$(t) discussed above with reference to FIGS. 2-3.

Photocurrent Photocurrent$_2$(t)—generated by the second photodetector 260B is converted by a "first cascade" operational amplifier U2 from a "current analog signal" Photocurrent$_2$(t) to a "voltage analog signal" voltage$_2$(t)-Photocurrent$_2$(t) and voltage$_2$(t) are non-limiting examples of "second analog signals" A$_2$(t) discussed above with reference to FIGS. 2-3.

"Second cascade" operational amplified U3 (i) receives as an input voltage$_1$(t) and voltage$_2$(t), and outputs a signal that is MULT[voltage$_1$(t)–voltage$_2$(t)], which is the difference between voltage$_t$(t) and voltage$_2$(t) multiplied by a constant whose value is MULT. It is noted that MULT[voltage$_1$(t)–voltage$_2$(t)] is one example of A(t) discussed above with reference to FIGS. 2-3.

Figure 5:
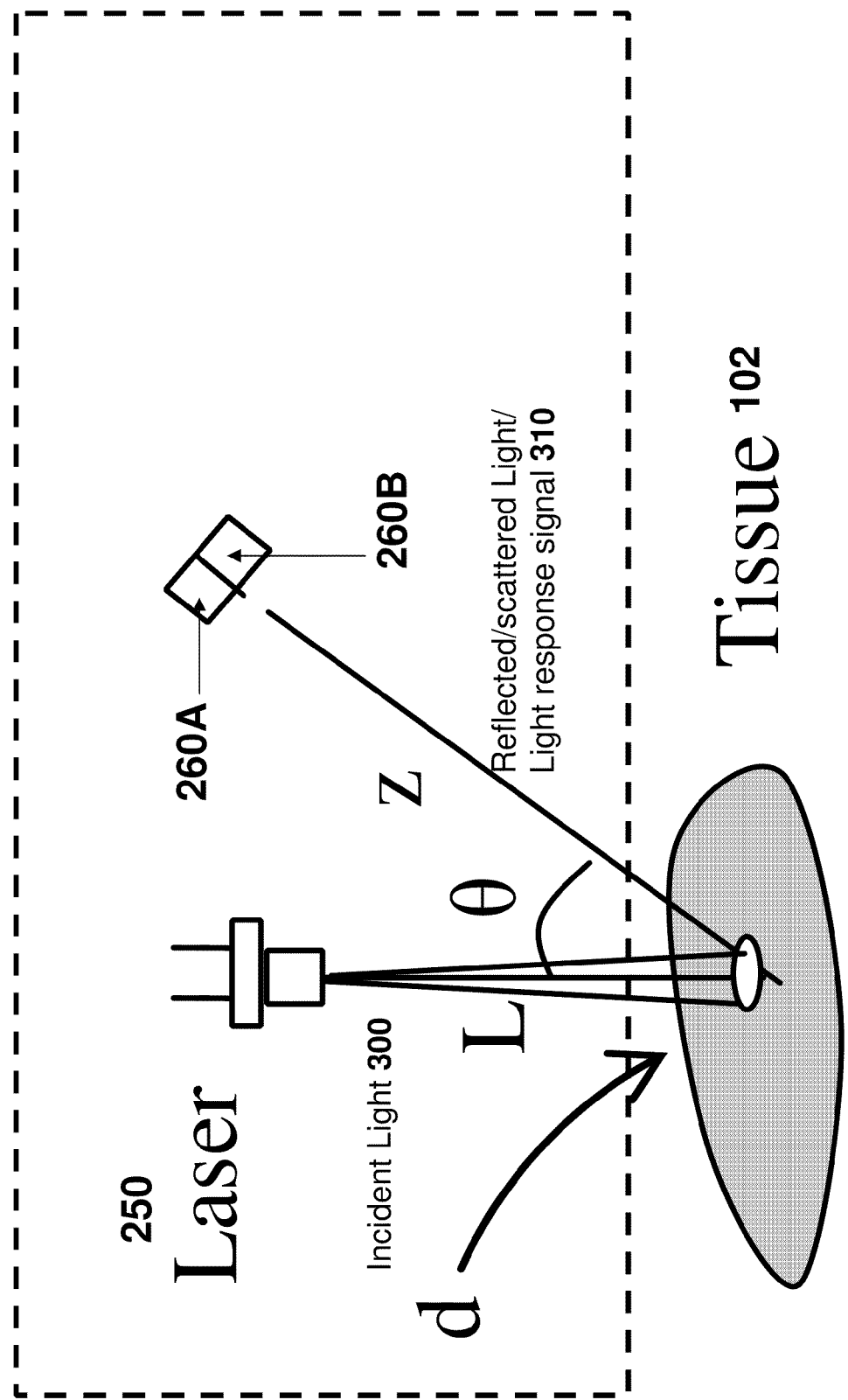
FIG. 5 is a diagram of a system for measuring blood parameter(s) including a coherent light source and a plurality of photodetectors.

A Discussion of FIG. 5

FIG. 5 is a diagram of a system for measuring blood parameter(s) including a coherent light source and a plurality of photodetectors. Light from a light source 300 is incident upon tissue 102 to produce a reflected/scattered light/light response signal 310 which is detected by the photodetectors 260.

In FIG. 5 the mean speckles size is:

$$\langle a \rangle = \frac{\lambda z}{d} \quad (Eq\ 5)$$

Where
λ—wavelength of the light.
z—distance between photodiode and the measured object.
d—laser spot diameter.

Approximately the number of the speckles on the active area S$_p$ of the photodiode 260 is:

$$N = \frac{S_p d^2}{\lambda^2 z^2} \quad (Eq\ 6)$$

The mean current, generated by each speckle size element of the photo detector, is:

$$\langle I_S \rangle = \frac{\langle I_p \rangle \lambda^2 z^2}{S_p d^2} \quad (Eq\ 7)$$

The mean (DC) photodiode current $\langle I_p \rangle$ forming by N currents $\langle I_s \rangle$ in compliance with Kirchhoff's current law. Each speckle area is an independent realization of the same stochastic process, so fluctuating (AC) parts of these currents connected by relation:

$$\langle i_p^2 \rangle = \sum_1^N \langle i_S^2 \rangle \text{ and } \langle i_p \rangle = \langle i_S \rangle \sqrt{N} \quad (Eq\ 8)$$

For one element it is possible to take advantage of Gaussian assumption, were satisfied $\langle i_s \rangle = \langle I_s \rangle$. By substituting (3) into (4) and by taking into account that $\langle I_p \rangle = \xi W S_p$, where W is a light's power flux, after simplification, it is possible to obtain:

$$\langle i_p \rangle = \frac{\xi W \lambda z}{d} S_p^{1/2} \quad (Eq\ 9)$$

That is, amplitude of the current fluctuation is proportionally to square root of detector surface. Note, that this relation valid in conditions, when the photodetector collects only a small part of scattered light. This relation can be used to optimize the signal to noise relation. The mean shot noise current from the photodetector is:

$$\langle i_o \rangle = \sqrt{2Be\langle I_p \rangle} \quad (Eq\ 10)$$

Where B—signal bandwidth (f$_2$–0), normalized to 1 Hz.
e—electron charge 1.6e-19 C
Dividing (5) to (6), we get:

$$SNR = \frac{\lambda z}{d} \sqrt{\frac{\xi W}{2Be}} \quad (Eq\ 11)$$

So SNR≠f(S$_p$) and proportionally depend of the square root of the power flux on the photodetector.

Figure 6:
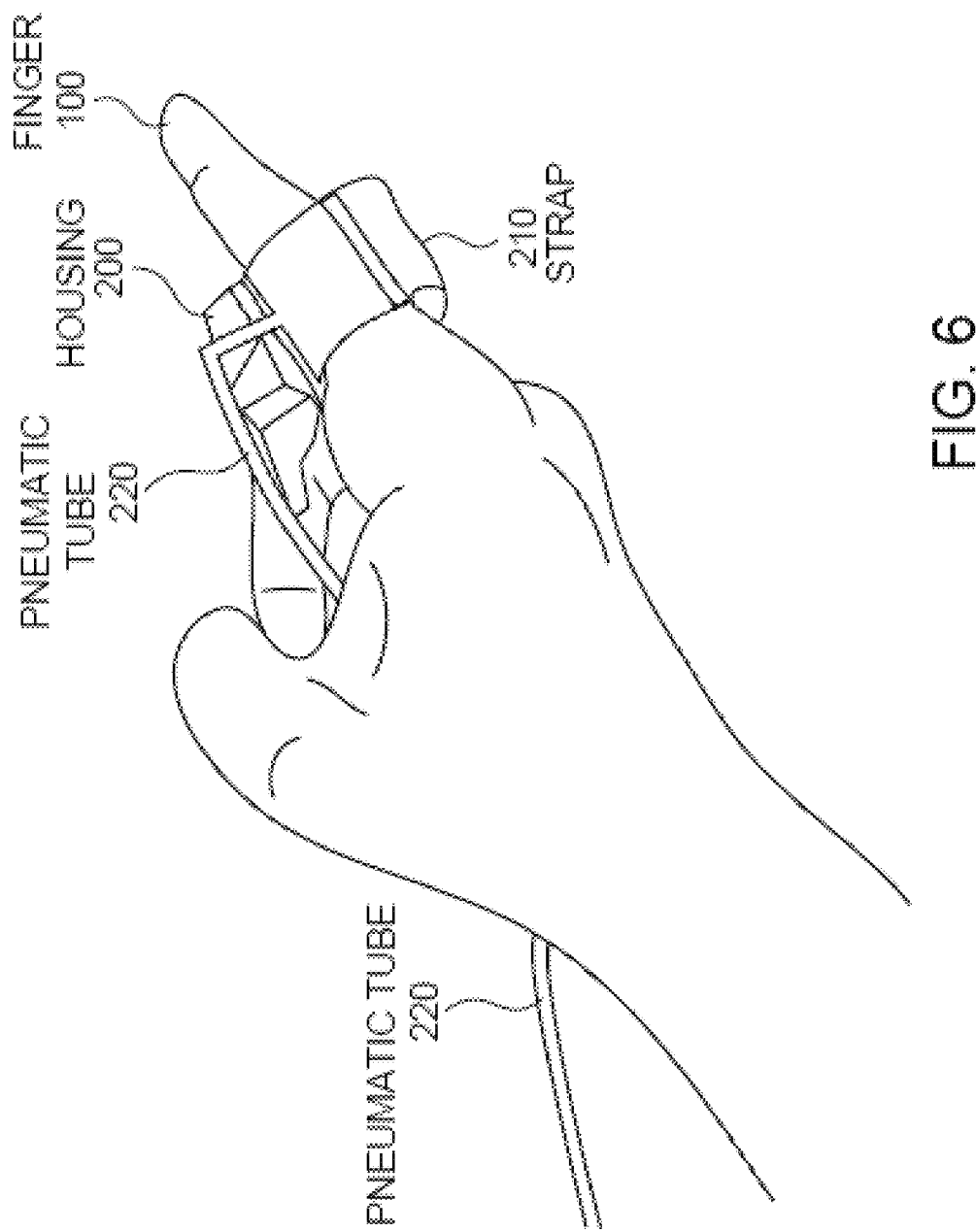
FIG. 6 is an illustration of an exemplary apparatus including a pneumatic tube deployed to a subject's finger.
Figure 7A:
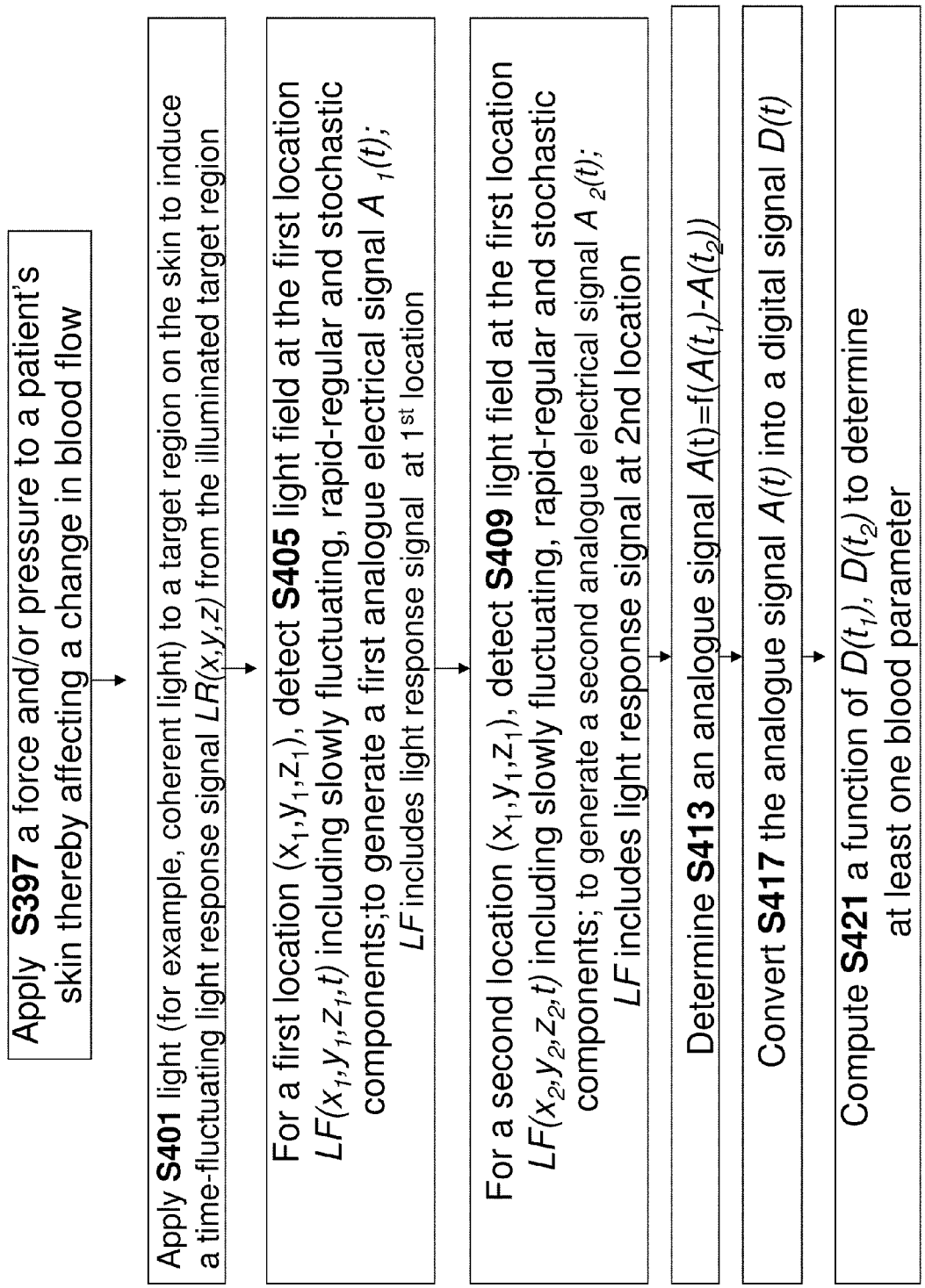
Figure 7B:
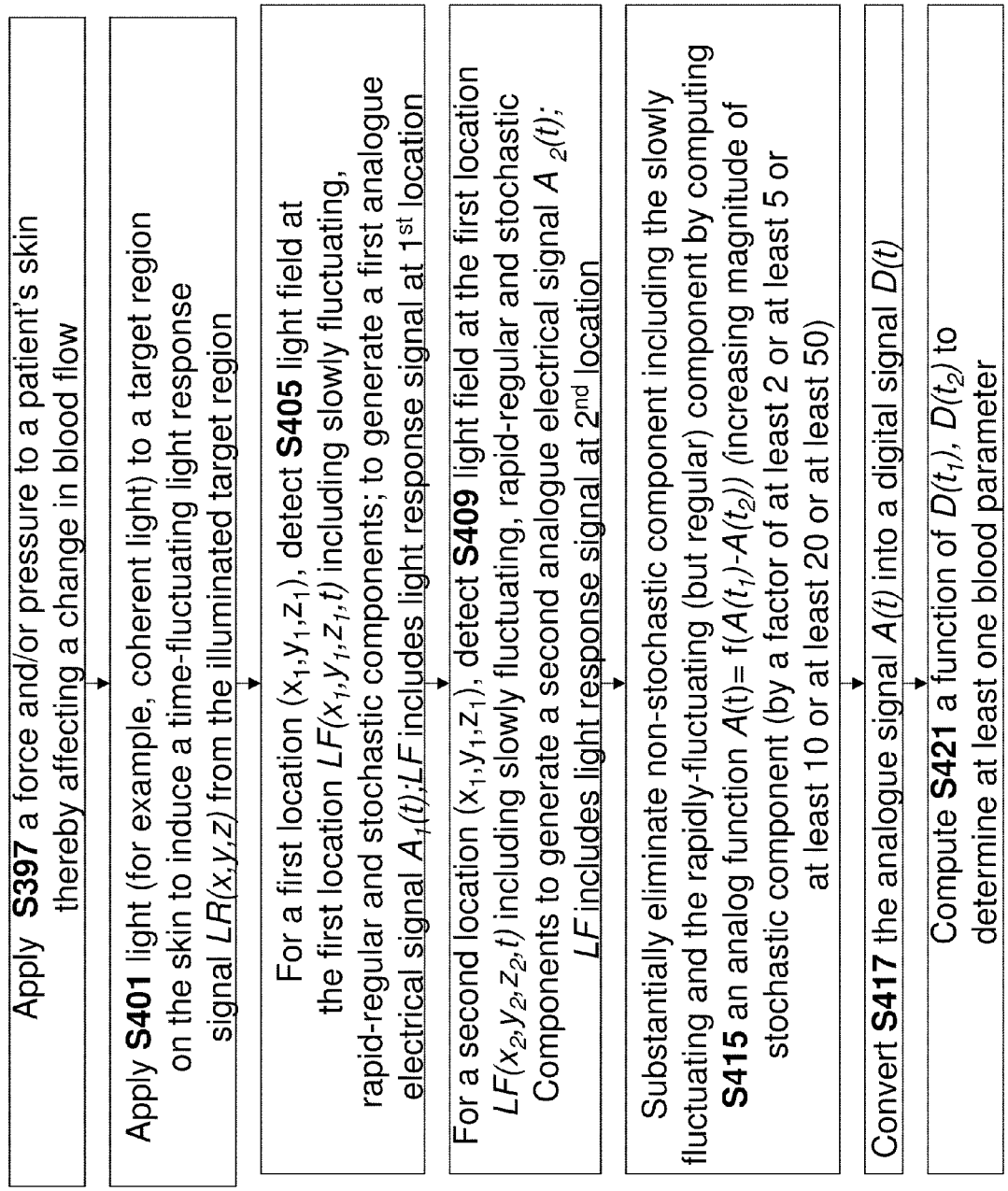
Figure 8:
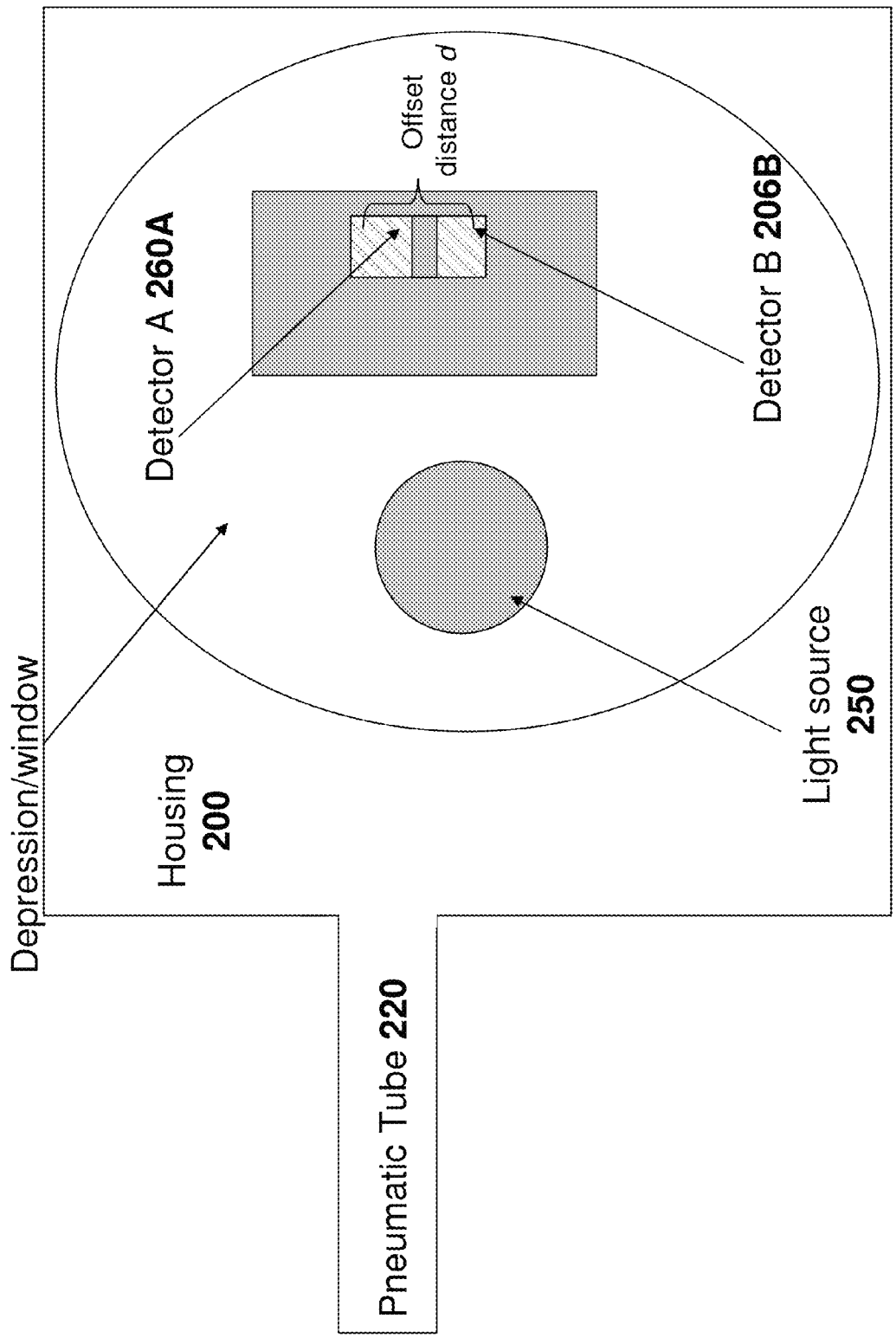
FIG. 8 is an illustration of the "underside" or "finger-facing surface" of the housing.

A Discussion of FIGS. 6-8: Embodiments where a Force and/or Pressure is Applied to a Subject's Skin and/or Tissue to Induce a Change in Blood Flow FIG. 6 is an illustration of an exemplary apparatus for: (i) inducing a change of blood flow in a subject's biological tissue (for example, in his/her finger or any other location on the subject's body); and (ii) generating an analog electric signal A(t) as discussed above. Towards this end, the apparatus of FIG. 6 includes a pneumatic tube 220 and a strap 210 that are mechanically coupled to a device housing 200. Pneumatic tube 220 and strap 210 together form a pressurizing assembly that is operative to induce a change in blood flow. In the non-limiting example of FIG. 6, the pressurizing assembly including pneumatic tube 220 and strap 210 are operative to induce a change in blood flow in the subject's fingers. In yet another embodiment, pressurizing assembly includes some sort of vacuum assembly operative to provide a 'negative pressure' to a subject's back, and to induce a change in blood flow in the subject's back.

FIG. 7A is like FIG. 3A except there is an extra step of applying a force S397 and/or pressure to a subject's biological tissue (for example, skin) to induce a change in blood flow. In some embodiments, carrying out this extra step before effecting the DLS measurement is useful for situations where it is desired to measure one or more of blood viscosity, blood particle size, and blood coagulation rate. Once again, the skilled artisan is directed to WO 2008/053474.

FIG. 7B is like FIG. 3B except there is an extra step of applying a force S397 and/or pressure to a subject's biological tissue (for example, skin) to induce a change in blood flow.

Figure 9:
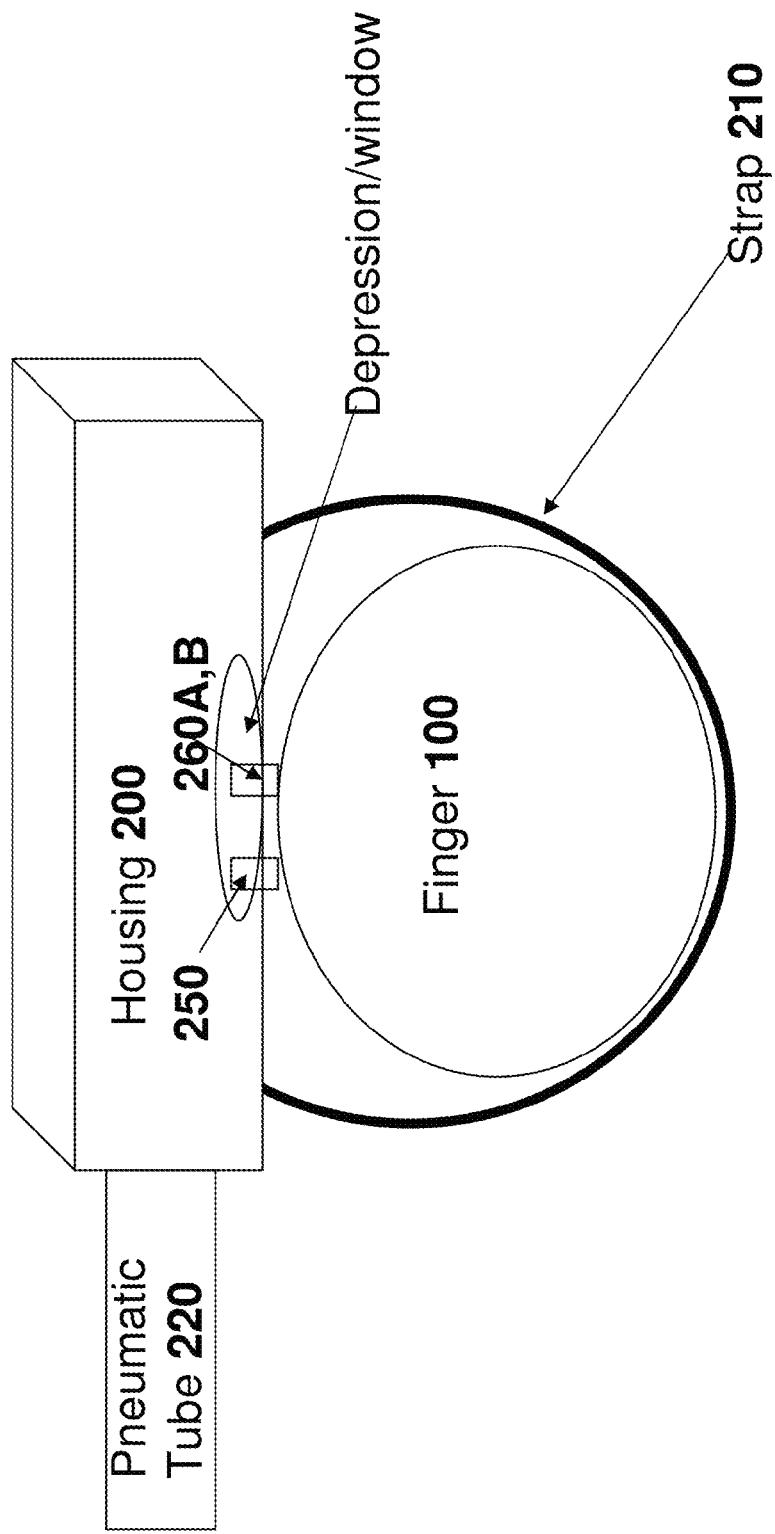
FIG. 9 provides a "cross-section view" of the apparatus of FIG. 6.

FIG. 8 is an illustration of the "underside" or "finger-facing surface" of housing 200. On this "lower, finger-facing surface" of housing 200 there is a depression and/or window, within which light source 250, and detectors 260A and 260B are situated. The skilled artisan is also directed to FIG. 9 which provides a "cross-section view" of the apparatus of FIG. 6.

A Discussion of FIG. 10—Embodiments Related to Optical Fiber

In the non-limiting example of FIG. 2, photodetectors 260A and 260B are separated by an "Offset distance" Off whose value is selected as discussed above—thus, photodetector 260A is located at position (x$_1$,y$_1$,z$_1$) and photodetector 260B is located at position (x2,y2,z2).

This is not a limitation. Alternatively, as shown in FIG. 10, photodetector 260A is located at a distance (for example, at least 1 or 3 or 5 or 10 cm) from ($x_1,y_1,z_1$) and receives the optical signal of the light field prevailing at ($x_1,y_1,z_1$) via optical fiber 290 and/or photodetector 260B is located at a distance (for example, at least 1 or 3 or 5 or 10 cm) from ($x_2,y_2,z_2$) and receives the optical signal of the light field prevailing at ($x_2,y_2,z_2$) via another optical fiber 290.

Figure 11A:
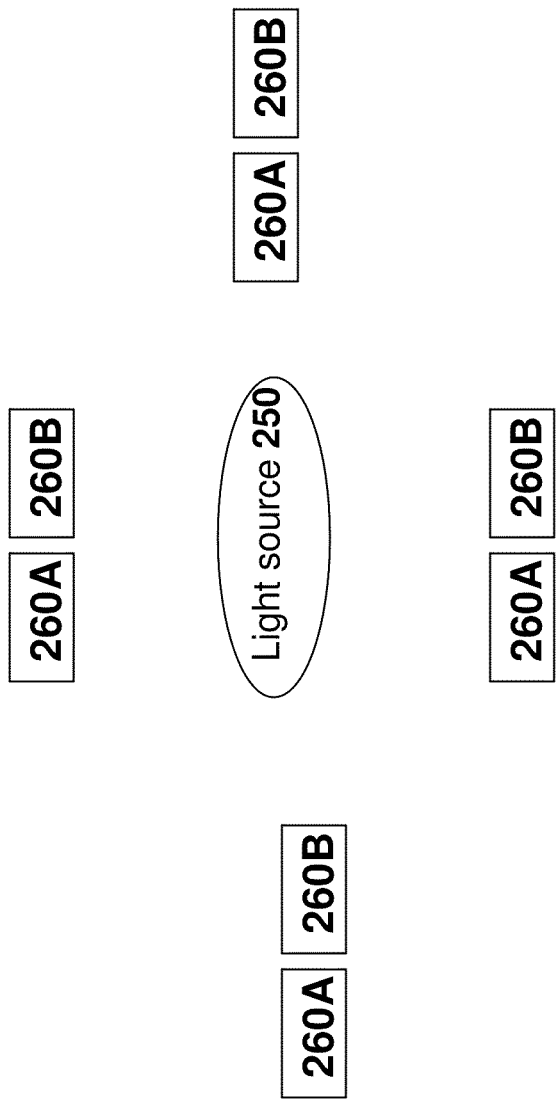
FIGS. 11A-11B illustrate an embodiment where more than one pair of photo detectors is provided.
Figure 11B:
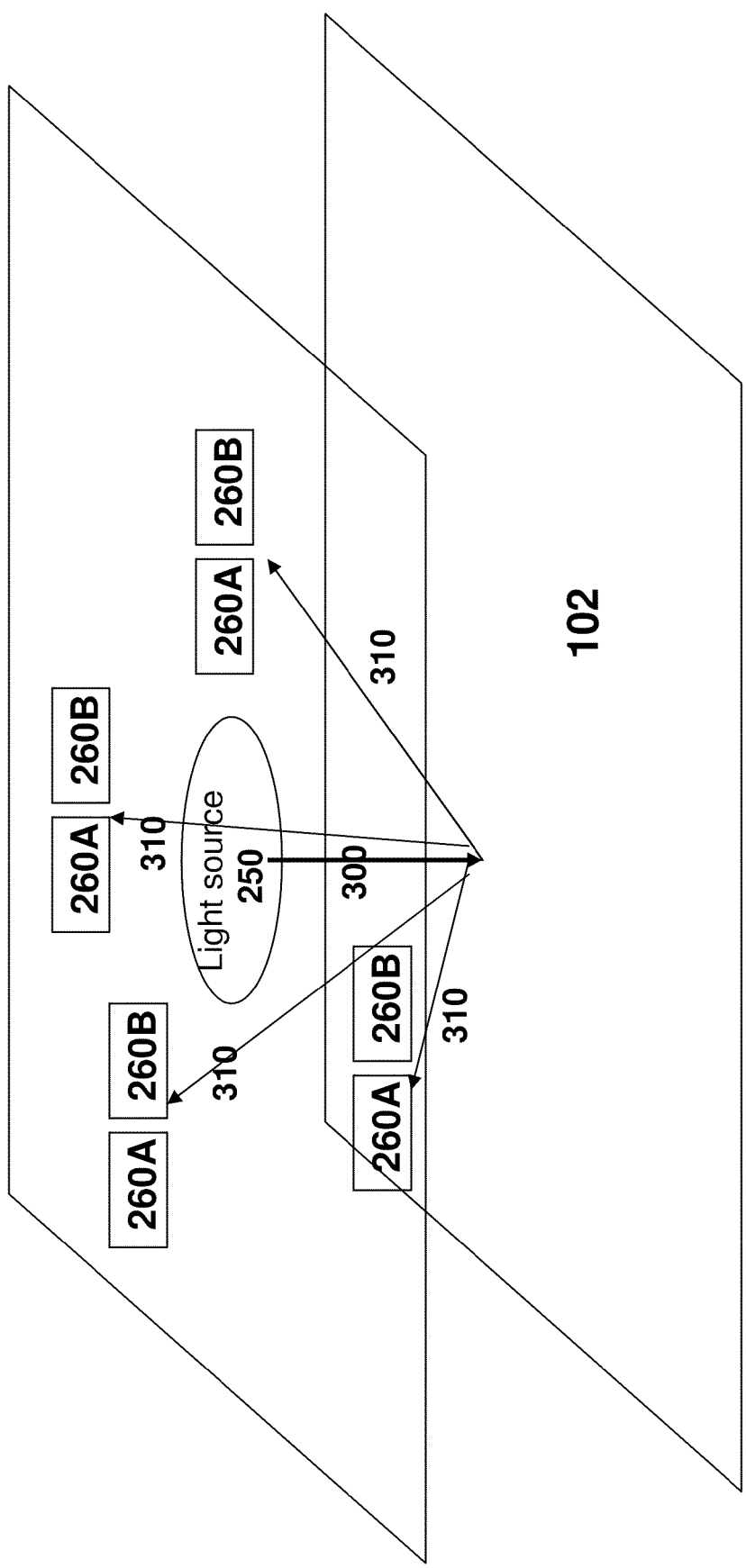

In some embodiments, as shown in FIGS. 11A-11B, more than one pair of photo detectors may be provided, and some sort of averaging between results associated with each pair of photodetectors may be computed, in order to determine a more accurate assessment of the subject's physiological parameter(s).

First Additional Discussion

In some embodiments, the behavior of a DLS related parameter ($d(\ln(G)/dt)$) utilized for the determination of systolic and diastolic blood pressure, where correlation function $G(\tau)$ of temporal intensity fluctuations of light scattered by moving particles is given by:

$$G(\tau) = \frac{<I(t) \cdot I(t+\tau)>}{<I(t)>^2}.$$

For example, there is a pressurizing cuff (for example, including pneumatic tube 210 and strap 220) is inflated up to over systolic pressure of 200 mm Hg during the first 5 seconds. Thereafter, for the next 75 seconds, the air pressure in the cuff is gradually reduced. Simultaneously, the DLS measurement is carried out at the area beneath the cuff. In this case, the parameter $d(Ln(G))/dt$ reaches its minimum point when the pressure measured in the cuff gets equal to the systolic pressure, as was defined previously by doing a standard blood pressure measurement test. Moreover, at the moment where the pressure in the cuff exceeds previously defined systolic pressure point, exactly at this point the value of parameter $d(Ln(G))/dt$ starts to increase gradually. Therefore, by identifying these two extreme points on the curve of $d(Ln(G))/dt$, both systolic and diastolic blood pressure can be measured optically. Naturally, all other functions mathematically related to autocorrelation parameters, can be used for blood pressure measurement.

This very unique sensitivity of DLS related parameters to the blood flow can be used for identification of blood flow disturbances or even for blood stasis identification and verification. To this end, any kind of a medical tool such as intro-vascular catheter (e.g. used for angioplasty) can be linked with DLS equipped optical fiber. Such a system is very efficient for identification of plugs and blood vessels abnormalities disturbing the normal blood flow.

Moreover, blood circulation parameters measured by DLS technique can by embedded as an inherent part of new emerging technology of biofeedback. Based upon the biofeedback technique, different body parameters including the blood flow that can be beneficial to control emotional status, cardiovascular training, rehabilitation and other purposes can be controlled. For example, such a system can be used for the control of blood flow during recovery from heart failure. In the biofeedback applications, DLS based measurement system can be combined with facilities affecting the mental status of a subject. For example, a method of binaural beats can be used. The binaural beats are resulted from the interaction of two different auditory impulses, originating in opposite ears. The binaural beat is not heard but is perceived as an auditory beat and theoretically can be used to entrain specific neural rhythms through the frequency-following response (FFR), i.e. the tendency for cortical potentials to entrain to or resonate at the frequency of an external stimulus. Thus, a consciousness management technique can be utilized to entrain a specific induction of sympathetic and parasympathetic system. More specifically, biofeedback system based on the methods of binaural beats can be governed by the parameters of flowing blood measured by means of DLS.

Second Additional Discussion

It is noted that in some embodiments related to FIG. 2 or other figures, photodetectors 260A and 260B may be (i) attached to housing 200 and/or (ii) integrally formed with housing 200 and/or (iii) rigidly maintained at a fixed distance from each other (for example, using housing 200).

Digital circuitry 280 or digital processing unit 280 may include any software/computer readable code module and/or firmware and/or hardware element(s) including but not limited to a CPU, volatile or non-volatile memory, field programmable logic array (FPLA) element(s), hard-wired logic element(s), field programmable gate array (FPGA) element(s), and application-specific integrated circuit (ASIC) element(s). Any instruction set architecture may be used in digital circuitry 280 including but not limited to reduced instruction set computer (RISC) architecture and/or complex instruction set computer (CISC) architecture.

In some embodiments, any feature or combination of features WO 2008/053474 (for example, detecting any physiological parameter disclosed in WO 2008/053474 or implanting any computational technique disclosed in WO 2008/053474 or any other feature disclosed in WO 2008/053474) may be provided.

All references cited herein are incorporated by reference in their entirety. Citation of a reference does not constitute an admission that the reference is prior art.

It is further noted that any of the embodiments described above may further include receiving, sending or storing instructions and/or data that implement the operations described above in conjunction with the figures upon a computer readable medium. Generally speaking, a computer readable medium may include storage media or memory media such as magnetic or flash or optical media, e.g. disk or CD-ROM, volatile or non-volatile media such as RAM, ROM, etc. as well as transmission media or signals such as electrical, electromagnetic or digital signals conveyed via a communication medium such as network and/or wireless links

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

What is claimed is:

1. A method for obtaining physiological information from a subject in accordance with a light field whose intensity varies according to location, the method comprising:
   a) applying partially or entirely coherent light to a target region of the subject to induce a light response signal from the illuminated target region which contributes to a location-dependent light field LF(x, y, z);
   b) detecting the light field LF($x_1, y_1, z_1$) prevailing at a first location ($x_1, y_1, z_1$) to generate a first analog electrical signal $A_1(t)$, the first analog electrical signal $A_1(t)$ including a dynamic light scattering (DLS) component DLS($A_1(t)$) that is indicative of a first DLS measurement;

c) detecting the light field signal $LF(x_2, y_2, z_2)$ prevailing at a second location $(x_2, y_2, z_2)$ to generate a second analog electrical signal $A_2(t)$, the second analog electrical signal $A_2(t)$ including a DLS component $DLS(A_2(t))$ that is indicative of a second DLS measurement and that is uncorrelated with the DLS component of the first analog signal $A_1(t)$;

d) processing, by analog electrical circuitry, the first and second analog electrical signals to generate a processed analog electrical signal processed(t) from a difference between the first and second analog electrical signals, wherein:

(i) a first DLS contribution ratio $$\frac{|DLS(A_1(t))|}{|A_1(t)|}$$

is defined as the ratio between a magnitude $|DLS(A_1(t))|$ of the DLS component of the first analog electrical signal and a magnitude $|A_1(t)|$ of the first electrical analog signal;

(ii) a second DLS contribution ratio $$\frac{|DLS(A_2(t))|}{|A_2(t)|}$$

is defined as the ratio between a magnitude $|DLS(A_2(t))|$ of the DLS component of the second analog electrical signal and a magnitude $|A_2(t)|$ of the second analog electrical signal;

(iii) processed analog electrical signal processed(t) includes a DLS component that is indicative of a combination of the first and second dynamic scattering measurements;

(iv) a processed signal DLS contribution ratio $$\frac{|DLS(\text{processed}(t))|}{|\text{processed}(t)|}$$

is defined as a ratio between a (i) magnitude $|DLS(\text{processed}(t))|$ of the DLS component of the processed analog electrical signal and (ii) a magnitude $|\text{processed}(t)|$ of the processed analog signal; and (v) the detecting and the processing are performed so that a ratio between:

i) the processed signal DLS contribution ratio $$\frac{|DLS(\text{processed}(t))|}{|\text{processed}(t)|};$$

ii) at least one of the first DLS contribution ratio $$\frac{|DLS(A_1(t))|}{|A_1(t)|}$$

and the second DLS contribution ratio $$\frac{|DLS(A_2(t))|}{|A_2(t)|}$$

is at least 10.

2. The method of claim 1 further comprising:
e) digitizing the processed analog signal to generate a digital signal indicative of a combination of the first and second dynamic scattering measurements;
f) processing the indicative digital signal to compute at least one physiological parameter.

3. The method of claim 2 wherein the computing includes computing at least one of a blood velocity, a blood rheological parameter, a blood pressure, a heartbeat, a blood oxygen concentration, and a pulse.

4. The method of claim 1 further comprising:
e) before the light field detecting, inducing a change in blood flow at or near the target region.

5. The method of claim 4 wherein the blood flow change inducing is carried out by applying a force or a pressure to the subject.

6. The method of claim 5 wherein the target region is located in a location selected from the group consisting of a finger region, a back region, a leg region, a face region and an arm region.

7. The method of claim 1 wherein a ratio between an intensity, at a wavelength of the at least partially coherent light, of the detected light field signal prevailing at the first location and intensity, at a wavelength of the at least partially coherent light, of the detected light field signal prevailing at the second location is between 0.95 and 1.05.

8. The method of claim 1 wherein the detecting at the first and second locations is performed respectively by first and second photodetectors.

9. The method of claim 8 wherein the first and second photodetectors are separated from each other by a separation distance that is at least 0.5 mm and at most 2 cm.

10. The method of claim 2 wherein the computing includes computing a blood rheological parameter.

11. The method of claim 2 wherein the computing includes computing a blood pressure.

12. The method of claim 2 wherein the computing includes computing a pulse.

* * * * *